United States Patent
Korman

(10) Patent No.: US 7,407,484 B2
(45) Date of Patent: Aug. 5, 2008

(54) PHYSIOLOGICAL MONITORING SYSTEM FOR A COMPUTATIONAL DEVICE OF A HUMAN SUBJECT

(75) Inventor: Ronen Korman, Petach Tikva (IL)

(73) Assignee: Medic4All Inc., Wilmington, DE (US)

( * ) Notice: Subject to any disclaimer, the term of this patent is extended or adjusted under 35 U.S.C. 154(b) by 446 days.

(21) Appl. No.: 10/472,752

(22) PCT Filed: Apr. 7, 2002

(86) PCT No.: PCT/IL02/00285

§ 371 (c)(1),
(2), (4) Date: Oct. 2, 2003

(87) PCT Pub. No.: WO02/080762

PCT Pub. Date: Oct. 17, 2002

(65) Prior Publication Data

US 2004/0152956 A1  Aug. 5, 2004

Related U.S. Application Data

(60) Provisional application No. 60/281,723, filed on Apr. 6, 2001.

(51) Int. Cl.
*A61B 5/00* (2006.01)
(52) U.S. Cl. ........................ 600/300; 600/310; 600/323; 600/481; 600/502
(58) Field of Classification Search ................. 600/300, 600/301, 309, 310, 323, 324, 481, 485, 502
See application file for complete search history.

(56) References Cited

U.S. PATENT DOCUMENTS 4,331,154 A    5/1982   Broadwater et al.

(Continued)

FOREIGN PATENT DOCUMENTS

DE           10005526         8/2001

(Continued)

OTHER PUBLICATIONS

Yang et al, "Development of the Ring Sensor for Healthcare Automation", *Robotics and Autonomous Systems*, 30:273-281, 2000.

(Continued)

*Primary Examiner*—Eric F Winakur

(57) ABSTRACT

A system for monitoring at least one physiological parameter of a human subject. The system of the present invention features a device with which the human subject regularly interacts, and which is connected to the computational device of the human subject for automatic collection of at least one physiological parameter which is also of medical interest. The device features at least one physiological sensor for collecting the measurement of the physiological parameter. The computational device of the human subject then preferably operates a software program to analyze the data which is collected, in order for the human subject to receive an alert when necessary. Alternatively or additionally, the collected data is sent to a remote computational device which is in communication with the computational device of the human subject for analysis. Optionally, the present invention enables the human subject to receive an alert if a deterioration in the physiological condition of the human subject is detected, thereby enabling the human subject to start preventive medical treatment with trained medical personnel as soon as possible. Thus, the awareness of the human subject about any incipient medical problem is immediately improved, which may result in an increased probability of being able to successfully treat and/or otherwise ameliorate those problems.

37 Claims, 3 Drawing Sheets

U.S. PATENT DOCUMENTS

| | | | |
|---|---|---|---|
| 4,407,295 A | | 10/1983 | Steuer et al. |
| 4,418,700 A | | 12/1983 | Warner |
| 4,758,579 A | | 7/1988 | Kohl et al. |
| 4,952,928 A | | 8/1990 | Carroll et al. |
| 5,045,839 A | | 9/1991 | Ellis et al. |
| 5,416,695 A | * | 5/1995 | Stutman et al. ............ 600/300 |
| 5,462,051 A | | 10/1995 | Oka et al. |
| 5,544,649 A | | 8/1996 | David et al. |
| 5,652,570 A | | 7/1997 | Lepkofker |
| 5,720,771 A | * | 2/1998 | Snell ............................ 607/60 |
| 5,741,217 A | * | 4/1998 | Gero ........................... 600/547 |
| 5,772,586 A | | 6/1998 | Heinonen et al. |
| 5,807,267 A | | 9/1998 | Bryars et al. |
| 5,853,005 A | | 12/1998 | Scanlon |
| 5,862,803 A | | 1/1999 | Besson et al. |
| 5,877,675 A | | 3/1999 | Rebstock et al. |
| 5,899,928 A | | 5/1999 | Sholder et al. |
| 5,917,415 A | | 6/1999 | Atlas |
| 5,990,866 A | * | 11/1999 | Yollin ......................... 345/157 |
| 6,046,761 A | | 4/2000 | Echerer |
| 6,134,504 A | | 10/2000 | Douglas et al. |
| 6,139,494 A | | 10/2000 | Cairnes |
| 6,413,233 B1 | | 7/2002 | Sites et al. |
| 6,491,647 B1 | | 12/2002 | Bridger et al. |
| 6,616,613 B1 | * | 9/2003 | Goodman .................... 600/300 |
| 2002/0045808 A1 | | 4/2002 | Ford et al. |

FOREIGN PATENT DOCUMENTS

| | | |
|---|---|---|
| EP | 0770349 | 5/1997 |
| EP | 0547000 | 2/2000 |
| EP | 1070479 | 1/2001 |
| GB | 2003276 | 3/1979 |
| WO | WO 96/01585 | 1/1996 |
| WO | WO 99/04685 | 2/1999 |
| WO | WO 00/40145 | 7/2000 |
| WO | WO 01/15056 | 3/2001 |
| WO | WO 01/97686 | 12/2001 |
| WO | WO 03/050642 | 6/2003 |
| WO | WO 03/050643 | 6/2003 |

OTHER PUBLICATIONS

Rhee et al, "Artifact resistant Power-Efficient Design of Finger-Ring Plethysmographic Sensors", *IEEE Transactions On Biomedical Enginering*, 48(7):795-805, 2001.

Yang et al, "A Twenty-Four Hour Tele-Nursing System Using a Ring Sensor", *Proc. Of 1998 Int. Conf. On Robotics and Automation*, Leuven, Belgium, pp. 387-392, 1998.

Rhee et al, "The Ring Sensor: A New Ambulatory Wearable Sensor for Twenty-Four Hour Patient Monitoring", *Proceedings of the 20th Annual International Conference of the IEEE Engineering in Medicine and Biology Society*, Hong Kong, 1998.

Mascaro, SA, "Photoplethymograph Fingernail Sensors for Measuring Finger Forces Without Haptic Obstruction", *IEEE Transactions On Robotics and Automation*, 17(5):698-708, 2001.

Yang et al, "Cuff-less Continuous Monitoring of Beat-to-Beat Blood Pressure Using Sensor Fusion", available through http://web.mit.edu/zyi/www/pdf/IEEETRans2000.pdf as of Dec. 9, 2001.

Yang et al, "Sensor Fusion for Noninvasive Continuous Monitoring of Pulsating Blood Pressure Based on an Arterial Hemodynamic Model", available through http://www.mit.edu/afs/athena.mit.edu/user/z/y/zyi/www/pdf/ASME99.pdf.

* cited by examiner

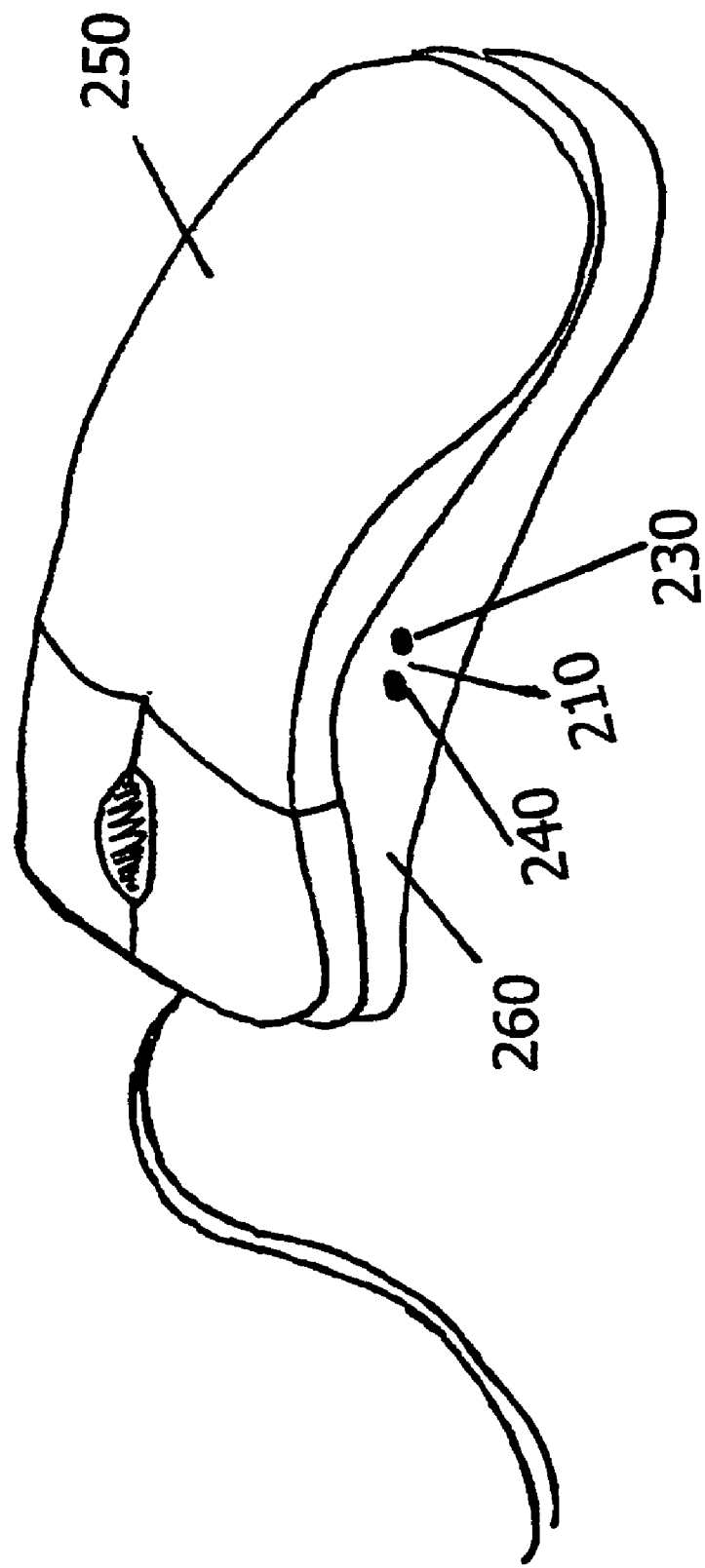

PHYSIOLOGICAL MONITORING SYSTEM FOR A COMPUTATIONAL DEVICE OF A HUMAN SUBJECT

RELATED PATENT APPLICATION

This application is a National Phase Application of PCT/IL02/00285, International Filing Date Apr. 7, 2002, which claims priority from U.S. Provisional Pat. Application Ser. No. 60/281,723 filed Apr. 6, 2001.

FIELD OF THE INVENTION

The present invention is of a method and apparatus for monitoring at least one physiological parameter of an individual through an interaction of the individual with a computational device. More specifically, the present invention is of an apparatus which features at least one physiological sensor for monitoring one or more physiological parameters, in which the apparatus is in communication with the computational device of the human subject and in which the data collected by the apparatus is processed and analyzed by a software program operated by the computational device of the human subject. This apparatus is preferably formed as a component of a peripheral device for the computational device of the human subject, such that the human subject interacts with the apparatus or device of the present invention as part of the normal operation of the computational device.

BACKGROUND OF THE INVENTION

Currently, a number of different types of devices are available for monitoring human subjects in a non-invasive manner. For example, heart function and respiration can be monitored in a patient through the use of electrodes which must be attached to the skin of the patient. Although non-invasive, such equipment is nevertheless uncomfortable for the patient, who must remain still while being monitored and who is attached to a network of sensors. In addition, such equipment is very expensive, limiting its use to hospitals and other medical settings in which both the cost and the discomfort of the patient can be justified. Furthermore, patients may become anxious when examined by medical personnel, thereby significantly altering the normal readings for these patients.

However, there are many different situations in which non-invasive monitoring of a human subject is desired. For example, such monitoring could be very useful as part of the overall health maintenance of the human subject, and could be used in order to detect a deterioration in the physiological condition of the subject before a concomitant deterioration in the health of the subject becomes noticeable. Examples of adverse physiological conditions which could be detected with regular non-invasive monitoring include but are not limited to excessive weight gain or less; arrhythmia and other heart conditions; incipient diabetes in the form of improper glucose metabolism; and loss of lung capacity or other problems with respiration.

In order to support regular monitoring of human subjects in their normal environment, such as in the home and at the office for example, the equipment must be non-invasive and easy to use. The equipment would then be able to monitor at least one physiological parameter of the human subject, without requiring the human subject to perform any complicated actions and/or to operate complex devices. Indeed, it would be highly preferred for the equipment to be incorporated as part of the regular daily living routine of the subject, since the requirement for any additional or special actions on the part of human subject is likely to result in decreased compliance. In addition, the equipment should be robust yet inexpensive. Furthermore, the equipment should be able to analyze data which is collected as part of the monitoring of the physiological parameter, or at least should be able to transmit such data to a remote computational device for analyzing the data. Unfortunately, such equipment is not currently available.

SUMMARY OF THE INVENTION

The background art does not teach or suggest a system or device for non-invasive monitoring of the human subject, which does not require any special action on the part of the human subject in order for the physiological measurements to be made.

There is thus a need for, and it would be useful to have, a system for non-invasive monitoring of a human subject, which is simple and easy to use, yet which is robust and which is preferably present as part of the daily living routine of the human subject.

The system of the present invention overcomes these deficiencies of the background art by providing a device with which the human subject regularly interacts, and which is in communication with the computational device of the human subject for automatic collection of at least one physiological parameter which is also of medical interest. The device features at least one physiological sensor for collecting the measurement of the physiological parameter, and preferably also features a data acquisition unit for digitally acquiring the sensor's output, an optional processing unit and a communication unit for transferring the data into the computational device. The computational device of the human subject then preferably operates a software program to process and analyze the data which is collected. Preferably, the data is stored on a log file or a database within the non-volatile memory of the computational device. Alternatively or additionally, the collected data is sent to a remote computational device which is in communication with the computational device of the human subject for analysis. Optionally, the present invention enables the human subject to receive an alert if a deterioration in the physiological condition of the human subject is detected, thereby enabling the human subject to start preventive medical treatment with trained medical personnel as soon as possible. Thus, the awareness of the human subject about any incipient medical problem is immediately improved, which may result in an increased probability of being able to successfully treat and/or otherwise ameliorate those problems.

According to the present invention there is provided a system for non-invasive monitoring of a human subject, comprising: (a) a peripheral device for contacting the human subject; (b) a sensor for being contained within the peripheral device, the sensor collecting data about a physiological parameter of the human subject; and (c) a host computational device for controlling the peripheral device and for receiving the data from the sensor.

According to another embodiment of the present invention there is provided a system for non-invasive monitoring of a human subject, comprising: (a) a peripheral device for contacting the human subject; (b) a sensor for being contained within the peripheral device, the sensor collecting data about a physiological parameter of the human subject; (c) a processing unit for being contained within the peripheral device for data analysis and (d) a host computational device for controlling the peripheral device and for receiving the data analysis from the processing unit.

According to yet another embodiment of the present invention there is provided a system for non-invasive monitoring of a human subject, comprising: (a) a wearable device for being in physical contact with the human subject; (b) a sensor for being contained within the device, the sensor collecting data about a physiological parameter of the human subject; (c) a processing unit for being contained within the device for control and for data analysis; and (d) a host computational device for receiving the data analysis from the processing unit.

Hereinafter, the term "wearable device" includes, but is not limited to, a sensing device fastened to the human subject at the wrist with a fastening article such as a bracelet, or fastened to the human subject's ear, arm or chest with appropriate fastening articles, or otherwise being in direct physical contact with and also being attached to the human subject, wherein the device is portable. Hereinafter, the term "contained within" also includes being attached to, integrally formed with or otherwise being in direct physical contact with.

The term "physiological sensor" refers in this connection to any sensor, optionally with a processing unit, which is suitable for measuring the physiological vital signs of the user or any standard medical equipment (such as automatic blood pressure device, ECG device and so forth, for example), that is capable of delivering output signal(s) and/or processed data via a data line or wireless link to the system on a main server and/or to a local data processing unit. Non-limiting, illustrative examples of such a sensor include a piezoceramic transducer, a piezoelectric transducer, a bio-impedance meter, a resistive strain gauge and a pressure sensor with fiber-optic components.

Examples of physiological functions and medical information which may optionally be monitored by the present invention include, but are not limited to: heart rate, arrhythmia, heart rate variability, ECG, blood pressure, body temperature and respiration rate. As used herein, the term "physiological parameter" refers to a signal which is received from a sensor and/or medical instrument, while the term "medical information" refers to the information which may be extracted or otherwise obtained by analyzing this signal and/or a combination of signals.

Hereinafter, the term "computational device" includes, but is not limited to, personal computers (PC) having an operating system such as DOS, Windows™, OS/2™ or Linux; Macintosh™ computers; computers having JAVA™-OS as the operating system; and graphical workstations such as the computers of Sun Microsystems™ and Silicon Graphics™, and other computers having some version of the UNIX operating system such as AIX™ or SOLARIS™ of Sun Microsystems™; the Palm OS; embedded operating systems for mobile telephones, as well as WAP-enabled devices and other cellular telephone devices which are able to receive content through the Internet, or any cellular telephone device which communicates according to the I-mode protocol (Japanese packet-based cellular telephone communication protocol) or UMTS (Universal Mobile Telecommunications System; also a mobile device communication protocol); or any other known and available operating system.

The method of the present invention could be described as a series of steps performed by a data processor, and as such could optionally be implemented as software, hardware or firmware, or a combination thereof. For the present invention, a software application could be written in substantially any suitable programming language, which could easily be selected by one of ordinary skill in the art. The programming language chosen should be compatible with the computational device (computer hardware and operating system) according to which the software application is executed. Examples of suitable programming languages include, but are not limited to, Visual Basic, Visual C, C, C++ and Java.

BRIEF DESCRIPTION OF THE DRAWINGS

The invention is herein described, by way of example only, with reference to the accompanying drawings, wherein:

FIGS. 2A and 2B show realizations of a mouse as an exemplary peripheral device according to the present invention.

DESCRIPTION OF THE PREFERRED EMBODIMENTS

Figure 1:
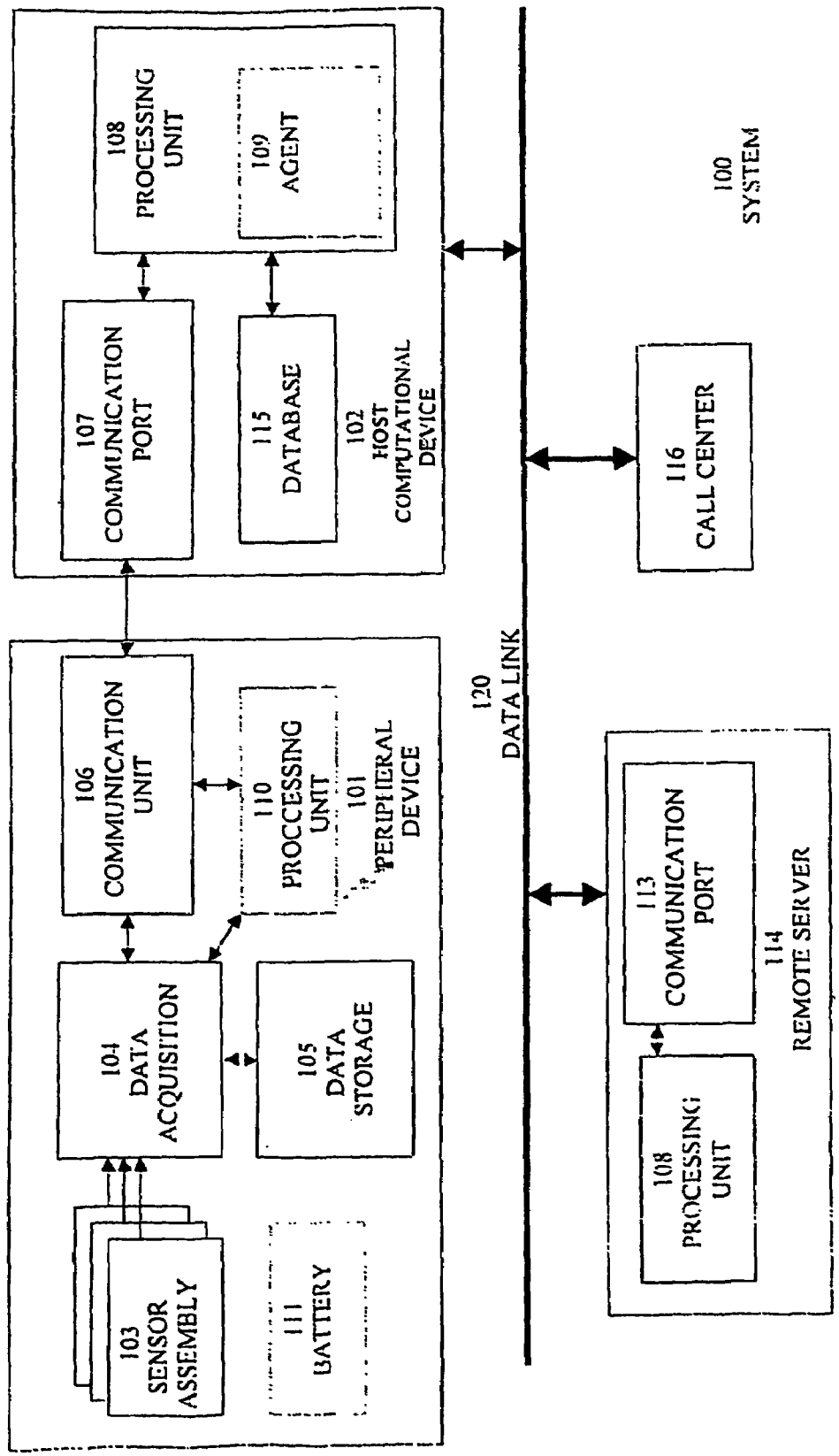
FIG. 1 is a schematic block diagram of a system according to the present invention.

The system of the present invention features a device with which the human subject regularly interacts, and which is in communication with the computational device of the human subject for automatic collection of at least one physiological parameter which is also of medical interest. The device features at least one physiological sensor for collecting the measurement of the physiological parameter, and preferably also features a data acquisition unit for acquiring the sensor's output, an optional processing unit and a communication unit for transferring the data into the computational device. The computational device of the human subject then preferably operates a software program to process and analyze the data which is collected. The software program and/or another such program optionally and more preferably stores the data on a log file or a database, enabling the human subject or medical personnel to view the data when requested. Alternatively or additionally, the collected data is sent to a remote computational device which is in communication with the computational device of the human subject for analysis. The present invention optionally enables the human subject to receive an alert if a deterioration in the physiological condition of the human subject is detected, thereby enabling the human subject to start preventive medical treatment with trained medical personnel as soon as possible. Thus, the awareness of the human subject about any incipient medical problem is immediately improved, which may result in an increased probability of being able to successfully treat and/or otherwise ameliorate those problems.

According to a preferred embodiment of the present invention, the physiological sensor for the device of the present invention is incorporated into a peripheral device which is part of the normal operation of the computational device of the human subject. Therefore, this peripheral device is more preferably a device which is frequently or regularly used by the human subject when operating the computational device, such that the measurements are obtained without conscious intent of the human subject and also without interfering with the work of the human subject. One highly preferred but non-limiting example of a suitable peripheral device into which the sensor is incorporated is a mouse or other pointing device, or a keyboard, or a mouse pad or resting place thereof, with which the human subject must frequently interact for the normal operation of the computational device. This peripheral device may optionally send a command to the computational device from the human subject, for example by "clicking on" or otherwise selecting an icon with a mouse or other pointing device by the human subject. Other illustrative, non-limiting examples of suitable peripheral devices include the chair on which the human subject sits (or any portion of that chair thereof), a pen or any other writing instrument of the human subject, a telephone, or any other object which is grasped or otherwise handled or manipulated by the human subject, or which is in physical contact with the human subject as part of a regular task performed by the human subject, such that the peripheral device is not handled by the human subject solely for the purpose of performing the physiological measurement to obtain the physiological parameter.

Alternatively, the peripheral device may only be in at least physical proximity to the human subject, although this is less preferred. Such an embodiment may optionally be implemented if the sensor within the peripheral device is capable of performing the physiological measurement without direct physical contact with the subject (for example, through a optical sensor).

According to another optional embodiment of the present invention, the peripheral device is implemented as a wearable device, as previously described. For example, the physiological sensor for the device of the present invention is optionally incorporated into a wrist watch as disclosed in U.S. patent application Ser. No. 10/006,357, filed on Dec. 10, 2001, having at least one inventor in common and being owned in common with the present application, which is hereby incorporated by reference as if fully set forth herein. The application discloses wrist wearable sensor capable of acquiring physiological parameters of the human subject and communicating with a gateway device preferably through a wireless communication channel. The computational device of the human subject serves as a gateway in the present invention.

In any case, the peripheral device may optionally be in wireless and/or wired communication with the host computational device. Wireless communication may optionally be performed through any type of signals, including but not limited to, radiowaves, infrared signals and signals transmitted and received according to Bluetooth protocol-enabled technologies, as a wireless communication channel. Wired communication may optionally be performed through any type of physical connector, such as a cable for example, as a wired communication channel.

The use of such a peripheral device for collecting the data about the physiological parameter is particularly preferred as it enables the present invention to obtain very accurate measurements of the physiological data, since the peripheral device is in close proximity to the human subject during normal operation of the computational device. Indeed, during the normal operation of a mouse or other pointing device, the human subject would tend to maintain physical contact with the peripheral in which the sensors are hidden, and would thereby have direct, frequent and regular contact with the sensors.

The peripheral device also preferably features a processing unit for preliminary data analysis of the data collected by the sensor.

The peripheral device would also preferably feature a wire or wireless data transmission link to the data processing unit of the computational device of the human subject. A software program on the computational device of the human subject would then monitor the physiological measurements of the human subject, optionally and preferably by performing an algorithm in order to obtain information of medical interest and relevance from the received data and then by storing the data in a log file or a database. More preferably, the software program would issue an alert whenever necessary. Alternatively, as previously noted, the results of the physiological measurements could optionally be transmitted to a remote computational device (for example through an Internet protocol) for analysis and more preferably for storage. Optionally and most preferably, such data is provided to a human operated call center, also most preferably with the medical information of the human subject. The call center may optionally have medically trained personnel, but in any case, preferably human personnel are able to receive and review at least the analyzed data, and more preferably also medical information and/or the medical history of the human subject.

According to an exemplary but preferred embodiment of the present invention, a monitoring system performs at least one physiological measurement of a human subject who is using his computational device through a peripheral device, such as a mouse, which features one or more physiological sensors. In addition, the system preferably features a software program, a microprocessor and a memory for handling and storing data related to the physiological parameter. For example, such a parameter could be representative of the heart rate and/or respiration rate and/or regularity of heart rhythm of the human subject as measured while operating the peripheral device. With a software monitoring the operation of physiological sensors placed inside a standard peripheral device (including but not limited to a keyboard, a mouse or a mouse pad) or alternately inside a wristwatch sensing device, measurements of the physiological parameter, such as the blood flow through the arteries and/or the infrared emission of the human body and/or the impedance of the human body, can be taken and transferred through a bi-directional or uni-directional communication link. At the computational device, a calculation can be made for extracting some medical parameters from this data, including but not limited to average heart rate, average respiration rate, regularity of heart rhythm, body temperature, $SpO_2$ level, $CO_2$ level, $O_2$ level and blood pressure). The results can then optionally and more preferably be displayed, stored and/or transferred to another computational device for further calculations, remote or otherwise, for example for constructing an automatic diagnosis of the human subject's health condition for example.

Most preferably, the data acquisition unit, the physiological sensors, the processing unit and the communication unit are permanently secured inside a standard peripheral device, which could then receive good physiological measurements of the human subject, as the human subject must physically contact the peripheral device during regular use of the computational device. Furthermore, the system of the present invention can optionally obtain operating power through the connection to the computational device, as for a USB (Universal Serial Bus) or RS232 based peripheral, or the keyboard's power for example.

The principles and operation of the system according to the present invention may be better understood with reference to the drawings and the accompanying description.

Referring now to the drawings, FIG. 1 is a schematic block diagram of a system according to the present invention. As shown, a system 100 features a peripheral device 101 for interacting with a human subject (not shown). Peripheral device 101 communicates with a host computational device 102, which is operated by the human subject. As explained in greater detail below, host computational device 102 is optionally and more preferably connected to a remote server 114 through a data link 120, which could optionally be the Internet for example. Alternatively, data link 120 could optionally be a direct dial-up connection, LAN connection, or a wireless method such as cellular connection between host computational device 102 and remote server 114.

Peripheral device 101 features at least one physiological sensor, preferably as part of a sensor assembly 103. Examples of such sensors include but are not limited to piezoceramic transducers, ultra sensitive piezoresistive sensors, hydrophone, ultra low pressure sensors, sensitive accelerometers or fiber-optic microphone sensors may optionally be used (such as for sensing the physiological vibration of the human subject). Additionally or alternately, thermistors, thermocouple sensors or/and infrared thermopile sensors may optionally be used (such as for sensing the temperature of the human subject). Infrared thermopile sensors have the advantage of not requiring direct physical contact between the skin of the human subject and the sensor.

Other examples of suitable non-invasive sensors include, but are not limited to, a bio-impedance meter (for sensing changes in the electrical impedance of the human subject), a photo-plethysmograph transducer (for sensing blood volume with an optical sensor), positioning sensor, a weight (for sensing the weight of the human subject), a $SpO_2$ sensor (for sensing partial oxygen pressure), $O_2$ sensor (for sensing oxygen levels in the blood), $CO_2$ sensor (for sensing carbon dioxide levels in the blood) and a glucose sensor (for sensing glucose levels in the blood).

Peripheral device 101 also preferably features an acquisition unit 104 and a data storage component 105 for at least temporarily storing data related to the measured physiological parameter. Optionally, peripheral device 101 also features a battery 111. Preferably, peripheral device 101 features a processing unit 108 for more preferably controlling one or more operations of peripheral device 101, but at least for controlling one or more operations of sensor assembly 103. Also, preferably processing unit 108 controls data analysis of collected data and a communication unit 106 for establishing bi-directional or unidirectional communication with host computer 102. Examples of communication unit 106 include but are not limited to, a wired—RS232 serial connection, USB connector or port, a Firewire™ enabled connector, communicator or port, a communicator, or a wireless—a dedicated RF protocol or connector or port operating according to the "Bluetooth"™ protocol or "Home RF"™ protocol, a communicator, connector or port operating according to the Infrared IRDA protocol, and a data connection operating according to the contact-less communication protocol.

Host computer 102 also preferably features a communication port 107 for receiving and transmitting data and/or other types of communication with communication unit 106.

Peripheral device 101 preferably maintains the same basic functional components as the original standard peripheral device, such as a computer mouse, a keyboard or a mouse pad (including but not limited to the WR511 product of 3M Inc., USA). Peripheral device 101 therefore maintains the original properties and functions of the basic peripheral device, but is also preferably equipped with additional components for the purpose of the current invention. An example of peripheral device 101 as incorporating such a standard peripheral device is shown in FIG. 2, which shows a mouse incorporating the additional components according to the present invention (see description below). These components optionally include but are not limited to, one or more sensors, a PCB card, a battery and an additional external cable for communication purposes. Peripheral device 101 preferably has its own unique serial number stored in data storage component 105 for initializing functions with host computational device 102 during the startup sequence.

After agent software 109 is installed into host computational device 102, agent software 109 determines through which communication port host computational device 102 communicates with peripheral device 101. In particular, agent software 109 determines the serial number and status of operation of peripheral device 101. Then, once host computational device 102 begins operations after startup, host computational device 102 preferably initiates activities of agent software 109. If however the human subject wishes to start the operation of agent software 109 manually (rather than automatically, for example from the startup sequence), agent software 109 would preferably only start operations upon the request of the human subject.

As agent software 109 starts working, agent software 109 tries to establishes a connection with peripheral device 101, until agent software 109 receives an acknowledge message from peripheral device 101. If, however, after a sufficiently long period of time peripheral device 101 does not acknowledge this communication, a malfunction is preferably declared and optionally a technical fault alert message is sent to the human subject. The period of time which is considered to be sufficiently long may optionally and more preferably be predetermined and/or determined by the human subject.

After establishing a communication link, agent software 109 examines peripheral device 101 for any malfunctions. In order to do so, agent software 109 more preferably asks peripheral device 101 to activate one of the available sensors 103, asking such a sensor 103 to perform a measurement. Next, peripheral device 101 preferably activates this sensor 103 and transfers the results to agent software 109. The measurement result is examined by agent software 109 for validity. Most preferably, this examination is performed with every sensor 103 within peripheral device 101.

Any failure during the above examination is preferably recorded into a log file, after which agent software 109 generates a message to the human subject. If available, preferably agent software 109 sends this message to a system administrator (not shown) at remote server 114 by using data link 120.

Then, preferably, agent software 109 searches for the human subject's identification information (which has more preferably been at initiation of operations). If, however, the operation system does not support such information, agent software 109 preferably initiates an identification process. Examples of suitable identification methods include but are not limited to, human subject's name and password; smart card; biometric sensors (such as fingerprint or iris scan sensor); and a contact less card (which enables only a specified human subject carrying such a contact less card to operate the computer, as the presence of this card is sensed only at close proximity to the computer, thereby identifying the human subject).

Optionally or alternately, the raw physiological data may be used to identify the human subject by using some unique characteristics of the human subject, such as the human subject's weight.

The human subject may optionally ignore the message and measurements could not be carried out, but after a predetermined period of time, agent software 109 preferably generates a message asking the human subject to be checked by peripheral device 101, since otherwise system 100 would not be able to collect sufficient data.

After identifying the human subject, agent software 109 sends a request to peripheral device 101 to start capturing measurements from the human subject.

Acquisition unit 104 of peripheral device 101, upon receipt of such a request, preferably activates one or more sensors 103. Sensors 103 begin collecting physiological data from the human subject.

Acquisition unit 104 preferably captures the data coming out from sensors 103, transferring the data back to agent software 109. Agent software 109 preferably examines the validity of the received data, for example in order to determine whether the data contains some indications of legitimate physiological data, or alternatively whether the data only contains noise. Acquisition unit 104 continues transferring data until agent software 109 determines that sufficient data is collected and preferably asks acquisition unit 104 to stop collecting data.

Agent software 109 preferably performs an algorithm for calculating some medical parameters from the raw data just received from peripheral device 101, including but not limited to, calculation of blood pressure, average heart rate, average breathing rate, and regularity of heart rhythm for example.

Agent software 109 may optionally ask peripheral device 101 to start capturing the human subject data in cases of ambiguity or when the medical parameters need to be re-analyzed. In this case, peripheral device 101 performs the sensing process again, transferring the additional data to agent software 109.

The calculated parameters and optionally the raw data are preferably stored in a log file or a database 115. Furthermore, agent software 109 preferably performs another algorithm for generating an alert if the medical parameters showed a value beyond the normal expected values.

There are more preferably three levels of alerts. The lowest level is only for malfunction reports of the device itself. The second level of alerts is for emergency alerts only, in which an alert is given if values for the calculated medical parameters falls beyond the normal values expected from a healthy human subject. The third and highest level is a full alert, which gives an alert to any degradation in the health of the human subject, according to any degradation in the physiological measurements of the human subject.

An alert message is preferably shown to, and/or otherwise brought to the attention of, the human subject, for example on the monitor of host computational device 102, or alternatively by any other methods available (including but not limited to a telephone conversation, an SMS (short message service) message and/or an e-mail message).

The medical parameters and/or the sensor measurements may be sent to remote server 114 whenever an on-line data link 120 is established. Host computational device 102 may also optionally encrypt and store all of those parameters in a non-volatile memory (such as a database on a permanent storage medium for example; not shown).

More preferably, parameters which are sent to remote server 114 are sent according to one or more security methods (for example "HIPA" guidelines) or protocols (for example, by using S.S.L, IPSEC or PKI methods) for maintaining the privacy of the human subject.

Agent software 109 may optionally receive software updates and parameters from remote server 114. Remote server 114 may then optionally ask agent software 109 to examine the human subject more often in order to improve the diagnostic quality. Agent software 109 may optionally receive system text updates for showing to the human subject through the monitor of host computational device 102. If host computational device 102 is equipped with a camera, the human subject may optionally engage in a video conference/conversation with one or more medical personnel in a contact center.

In order to acquire the physiological data needed for this invention, the device may optionally use one or more of several types of very accurate and sensitive sensors. One optional sensor is based on a photo-plethysmograph transducer (as discussed later), fiber optics, a piezo-ceramic transducer, piezo-electric transducer, low frequency hydrophone, an ultra low pressure sensor, a sensitive accelerometer, an impedance sensor (for measuring bio-impedance), an infrared thermopile sensor, a thermistor, a thermocouple sensor and/or piezo-resistive technology. These sensors are needed to acquire the physiological raw data for extracting those medical parameters needed to analyze the human subject's health.

One example of such a sensor is a photo-plethysmograph transducer, as described for example in "Medical Equipment Dictionary" by Malcolm Braun et al., The Institute of Medical and Dental Bioengineering, Royal Liverpool Hospital, United Kingdom (see http://www.thebrowns23.freeserve.co.uk/as of Apr. 3, 2002).

As its name suggests, this device measures volume by optical methods, particularly for detecting changes in blood perfusion in limbs and tissues. Light may be transmitted through a capillary bed such as in the ear lobe or fingertip. As arterial pulsations fill the capillary bed the changes in volume of the blood vessels modify the absorption, reflection and scattering of the light. This technique can be used to show the timing of events such as heart beats, but is less preferred for measuring changes in volume and is also very sensitive to motion artifacts.

A miniature tungsten lamp may optionally be used as the light source but the heat generated causes vasodilation which alters the system being measured. An infrared light-emitting diode (LED) of a suitable color (e.g. gallium arsenide LED) is preferred as it may produce a more accurate result.

Such a sensor may optionally be placed inside a computer mouse's left key or any other part being contacted by a finger, for example a side portion at which the finger holds the mouse, for example for measuring blood pulses at the fingertip of the human subject who is operating the mouse. These measurements are safe and non-invasive. Electrical or electrically conducting parts are not in contact with the skin of the patient. The power spectrum of both breathing (respiration) and heartbeat is almost entirely below 10 Hz, easily measured by this sensor.

Figure 2A:
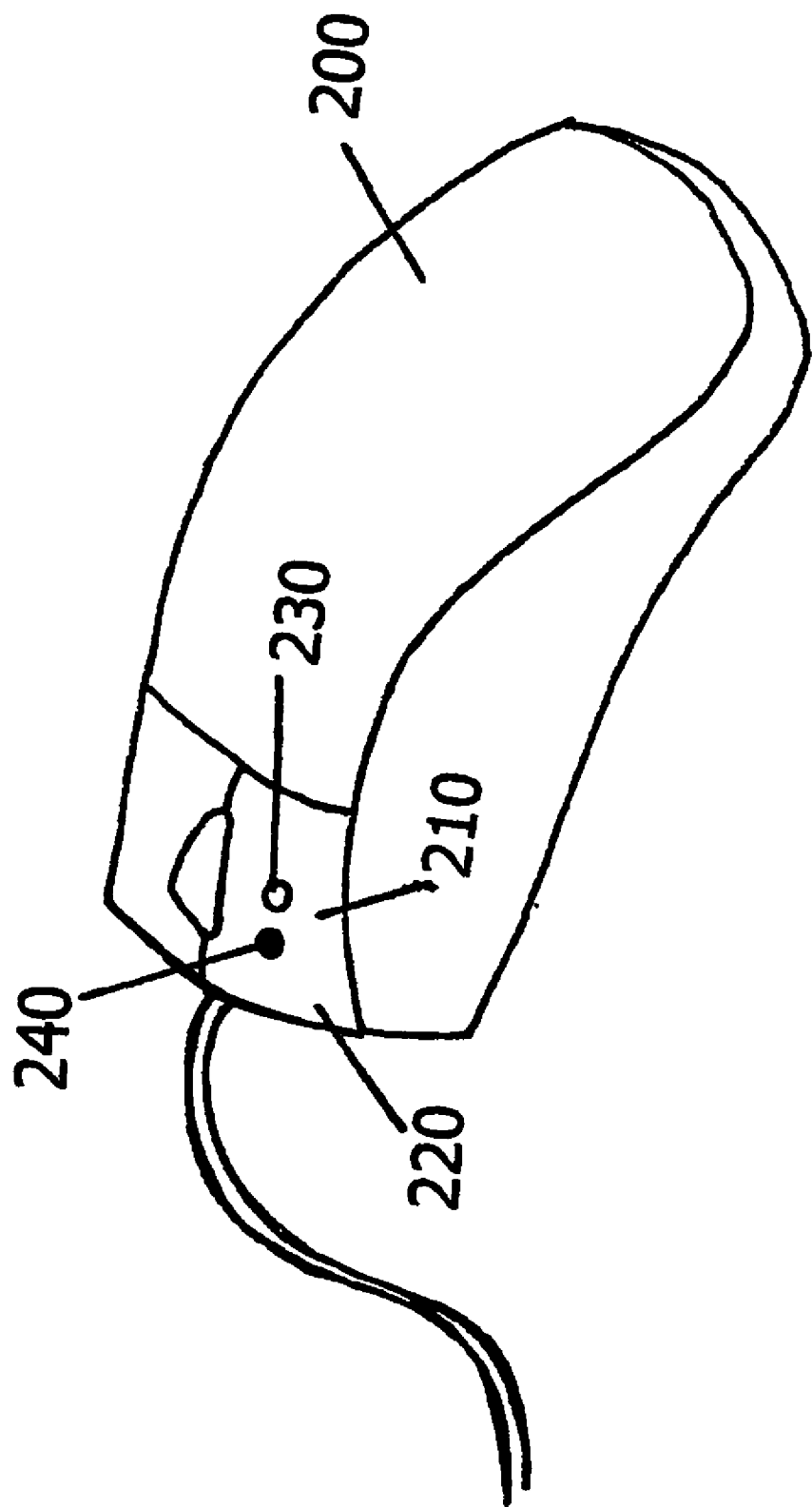

One exemplary implementation of the installation of the device according to the present invention in a computer mouse is shown with regard to FIG. 2. FIGS. 2A and 2B show two external views of a mouse which incorporates the additional components according to the present invention (see description below). As previously discussed, these components optionally include but are not limited to, one or more sensors, a PCB card, a battery and an additional external cable for communication purposes (these components are not shown in FIGS. 2A and 2B).

FIG. 2A shows a first exemplary implementation of a mouse 200 according to the present invention, which incorporates the device according to the present invention. As shown, mouse 200 preferably features a sensor 210, which more preferably contacts at least a portion of the finger of the human subject. Preferably, sensor 210 is located at a left mouse key 220 in order to facilitate such contact without requiring any special action by the human subject. More preferably, sensor 210 is a photo-plethysmograph transducer as previously described, featuring a light source 230 and a reflector 240. Light source 230 is as previously described. Reflector 240 receives the reflected light from the finger or other portion of the human subject, which is then used to determine the physiological parameter.

FIG. 2B shows a second embodiment of a mouse 250 according to the present invention, which again incorporates the device according to the present invention. Again, sensor 210 is more preferably a photo-plethysmograph transducer as previously described, again featuring light source 230 and reflector 240. Now however, sensor 210 is preferably located at a side 260 of mouse 250, such that a finger or other part of the human subject may again contact sensor 210 in order to facilitate such contact without requiring any special action by the human subject.

Extracting some medical parameters from the above sensor raw data can be done as explained by in U.S. Pat. No. 4,245,648, entitled "Method and apparatus for measuring blood pressure and pulse rate".

The disclosed system includes a sensor head which is coupled to an exteriorized artery. The sensor head includes electromechanical transducers at first and second locations which convert each periodic arterial pulse pressure wave passing the first and second locations into first and second periodic electrical waveforms. Electronic circuitry analyzes the first and second periodic electrical waveforms to determine the rise time of each periodic waveform produced by the first and second transducers. This electronic circuitry also analyzes the first and second periodic waveforms to determine the transit time of each pulse pressure wave between the first and second locations. An electronic computer utilizes the rise time and transit time data and certain calibration data to determine and display systolic pressure, diastolic pressure, and pulse rate immediately following each pulse pressure wave. The system of U.S. Pat. No. 4,245,648 also computes and displays fifteen beat moving average values of the systolic pressure and diastolic pressure. Other teachings of the background art which are hereby incorporated by reference as if fully set forth herein include U.S. Pat. Nos. 2,658,505; 3,132,643; 3,095,872; 3,734,086; and 2,114,578.

U.S. Pat. No. 2,658,505 discloses an arterial pulse wave velocity meter having a piezoelectric transducer which is coupled to an exteriorized artery. The transducer utilized in connection with this device generates electrical signals representative of the displacement of the artery wall and the rotational force imparted to a second element of the transducer. An electrical differentiating circuit is provided to obtain the rate of change of the displacement waveform. Additional circuitry is provided to measure the ratio between the differentiated values and the electrical signal created by torsional forces. This ratio is utilized to determine the velocity of the arterial pulse wave.

U.S. Pat. No. 3,132,643 determines blood pressure by measuring the time lapse between an electrocardiac signal generated by the heart and a consequent pressure pulse measured at a remotely located point on the body.

U.S. Pat. No. 3,095,872 measures blood pressure by impressing continuous wave alternating pressure signals on a flow of arterial blood. Phase changes in the continuous wave modulation signal between two points spaced along the arterial blood stream are measured to determine relative blood pressure levels.

U.S. Pat. No. 3,734,086 discloses an apparatus for detecting, measuring and displaying the pulse propagation time from the heart to an extremity by non-invasive means.

U.S. Pat. No. 2,114,578 discloses an apparatus for visibly indicating the frequency and amplitude of the human pulse. A rubber compression bag is used in combination with a piezoelectric crystal to convert blood pressure pulsations into electrical impulses.

It will be appreciated that the above descriptions are intended only to serve as examples, and that many other embodiments are possible within the spirit and the scope of the present invention.

What is claimed is:

1. A system for non-invasive monitoring of a human subject, comprising:
   (a) a peripheral device configured for physical contact with said human subject, said peripheral device being a user input device configured to allow said human subject to regularly interact with an autonomous computational device;
   (b) a sensor contained within said peripheral device, said sensor being configured for sensing said human subject and for automatically collecting data about a physiological parameter of said human subject without interfering with an action of said human subject, said action being performed during said interaction between human subject and said autonomous computational device;
   wherein said autonomous computational device is configured for being controlled by said peripheral device and for receiving said data from said sensor for monitoring said human subject; and said autonomous computational device comprises
   an agent software configured for being operated by said autonomous computational device and for analyzing said data from said sensor, wherein said agent software is configured to determine whether a physiological parameter of said human subject has deteriorated according to an analysis of said data, and wherein said agent software is configured to provide an alert message to said human subject if said physiological parameter has deteriorated.

2. The system of claim 1, wherein said peripheral device is contacted by said human subject during normal interactions with said autonomous computational device, such that said data is collected without requiring any additional action by said human subject.

3. The system of claim 1, further comprising:
   (e) at least one of:
   a remote server in communication with said autonomous computational device configured for receiving, processing arid storing said data wherein said agent software is configured to alert at least one of said human subject and an attendant associated with said remote server if said physiological parameter has deteriorated; and
   a manually operated call center configured for receiving said data and a medical history of said human subject and diagnosing said human subject according to said data and said medical history, wherein said agent software is configured to alert at least one of said human subject and an attendant associated with said call center if said physiological parameter has deteriorated.

4. The system of claim 3, wherein said alert message is automatically transmitted to said human subject.

5. The system of claim 1, wherein said peripheral device includes a device configured for transmitting at least one command of said human subject to said autonomous computational device for operating said autonomous computational device.

6. The system of claim 5, wherein said device is at least one of a computer keyboard and a computer pointing device.

7. The system of claim 6, wherein said computer pointing device is a computer mouse.

8. The system of claim 5, wherein said device is a touch sensitive screen.

9. The system of claim 1, wherein said peripheral device is in physical contact with said human subject while operating said autonomous computational device.

10. The system of claim 9, wherein said peripheral device is a mouse pad.

11. The system of claim 1, wherein said physiological parameter is selected from the group consisting of a blood pulse characteristic, blood pressure, heart rate, temperature, position, $SpO_2$ (saturation of peripheral oxygen), carbon dioxide level, glucose level and respiration rate.

12. The system of claim 1, wherein said sensor is selected from the group consisting of a SpO$_2$ (saturation of peripheral oxygen) sensor, carbon dioxide level sensor and a glucose sensor.

13. The system of claim 1, wherein said sensor is selected from the group consisting of a piezoresistive sensor, a hydrophone, an ultra low pressure sensor, an accelerometer, and a fiber-optic sensor.

14. The system of claim 1, wherein said sensor includes at least one photo-plethysmograph transducer, and at least one of blood pulse shape, blood pressure, heart rate and respiration rate is measured through said sensor.

15. The system of claim 1, wherein said sensor is selected from the group consisting of a thermistor, a thermocouple sensor, a positioning sensor and a weight sensor.

16. The system of claim 1, wherein said sensor includes at least an infrared thermopile sensor.

17. The system of claim 1, wherein said sensor includes at least a piezoceramic transducer.

18. The system of claim 1, further comprising a communication unit for communicating said measurement of said at least one physiological parameter to a physiological monitoring processing unit.

19. The system of claim 1, wherein said autonomous computational device is a general-purpose computer.

20. The system of claim 1, wherein said autonomous computational device is a physiological monitoring processing unit.

21. The system of claim 1, wherein said peripheral device is configured for a purpose other than physiological monitoring.

22. A system for non-invasive monitoring of a human subject according to claim 1 wherein said message comprises at least one member of the group consisting of: an identification of said physiological parameter, a description of a result of said analysis, a text message, a verbally audible message, an icon representing said physiological parameter, and an instruction to said subject to touch said sensor.

23. A system for non-invasive monitoring of a human subject, comprising:
(a) a user input device configured for being in physical contact with said human subject;
(b) a sensor contained within said user input device, said sensor being configured for sensing said human subject and for automatically collecting data about a physiological parameter of said human subject without interfering with an action of the user, said user input device configured for controlling an autonomous host computational device;
(c) a processing unit contained within said user input device configured for analyzing said data;
d) an autonomous host computational device configured for controlling said processing unit, receiving said data analysis from said processing unit, and receiving at least one command from said human subject through said user input device;
(e) an agent software installed on said autonomous host computational device and configured for being operated by said autonomous host computational device and for analyzing said data from said sensor, wherein said agent software is configured to determine whether a physiological parameter of said human subject has deteriorated according to an analysis of said data; and
(f) at least one of:
a remote server in communication with said host computational device, said remote server being configured for receiving, processing and storing said data, wherein said agent software is configured to provide an alert message to at least one of said human subject and an attendant associated with said remote server if said physiological parameter has deteriorated; and
a manually operated call center, configured for receiving said data and a medical history of said human subject, and diagnosing said human subject according to said data and said medical history, wherein said agent software is configured to provide an alert message to at least one of said human subject and an attendant associated with said call center if said physiological parameter has deteriorated.

24. The system of claim 23, wherein said host computational device controls said sensor through said processing unit.

25. The system of claim 23 wherein a said processing unit controls an operation of said sensor.

26. The system of claim 25, wherein said host computational device controls said sensor through said processing unit.

27. A system for non-invasive monitoring of a human subject according to claim 23, wherein said message comprises at least one member of the group consisting of: an identification of said physiological parameter, a description of a result of said analysis, a text message, a verbally audible message, an icon representing said physiological parameter, and an instruction to said subject to touch said sensor.

28. A method for non-invasive monitoring of a human subject through contact with a user input device, said user input device being in contact with a computational device, said method comprising:
providing a sensor being contained within said user input device, wherein said user input device is configured to allow said human subject to regularly interact with a host computational device;
physically contacting said user input device by at least a portion of said human subject, thereby sensing the human subject and automatically collecting data about a physiological parameter of said human subject by said sensor;
transmitting said data to said computational device;
controlling said sensor by said computational device;
analyzing said data from said sensor;
determining whether a physiological parameter of the human subject has deteriorated according to an analysis of said data; and
providing an alert message to the human subject if said physiological parameter has deteriorated.

29. The method of claim 28, wherein said contacting of said user input device further comprises: manipulating said user input device by said human subject to send at least one command to said computational device.

30. The method of claims 28, wherein said contacting of said user input device is performed while operating said computational device, without any additional action by said human subject being required.

31. The method of claim 28, further comprising:
providing at least one of:
a remote server in communication with said autonomous computational device configured for receiving, processing and storing said data wherein said agent software is configured to alert at least one of said human subject and an attendant associated with said remote server if said physiological parameter has deteriorated; and
a manually operated call center configured for receiving said data and a medical history of said human subject and diagnosing said human subject according to said data and said medical history, wherein said agent software is configured to alert at least one of said human subject and an attendant associated with said call center if said physiological parameter has deteriorated.

32. A method for non-invasive monitoring of a human subject according to claim 28, wherein said message comprises at least one member of the group consisting of: an identification of said physiological parameter, a description of a result of said analysis, a text message, a verbally audible message, an icon representing said physiological parameter, and an instruction to said subject to touch said sensor.

33. A system for non-invasive monitoring of a human subject, comprising:
  (a) a user input device configured for being in physical contact with said human subject;
  (b) a sensor contained within said user input device, said sensor being configured for sensing said human subject and for automatically collecting data about a physiological parameter of said human subject;
  (c) a processing unit contained within said user input device for control and for data analysis, such that said processing unit controls an operation of said sensor; and
  (d) a host computational device configured for receiving said data analysis from said processing unit, wherein said user input device is configured to allow said human subject to regularly interact with said host computational device;
  wherein said system is configured to determine whether said analyzed data indicates that said physiological parameter of the human subject has deteriorated; and
  wherein said system is configured to provide an alert message to said human subject if said physiological parameter has deteriorated.

34. The system of claim 33, further comprising:
  (e) at least one of:
  a remote server in communication, with said autonomous computational device configured for receiving, processing and storing said data wherein said agent software is configured to alert at least one of said human subject and an attendant associated with said remote server if said physiological parameter has deteriorated; and
  a manually operated call center configured for receiving said data and a medical history of said human subject and diagnosing said human subject according to said data and said medical history, wherein said agent software is configured to alert at least one of said human subject and an attendant associated with said call center if said physiological parameter has deteriorated.

35. A system for non-invasive monitoring of a human subject according to claim 33, wherein said message comprises at least one member of the group consisting of: an identification of said physiological parameter, a description of a result of said analysis, a text message, a verbally audible message, an icon representing said physiological parameter, and an instruction to said subject to touch said sensor.

36. A system for non-invasive monitoring of a human subject, comprising:
  (a) a peripheral device configured for physical contact with said human subject, said peripheral device being a user input device configured to allow said human subject to regularly interact with an autonomous computational device;
  (b) a sensor contained within said peripheral device, said sensor being configured for sensing said human subject and for automatically collecting data about a physiological parameter of said human subject without interfering with an action of said human subject, said action being performed during said interaction between human subject and said autonomous computational device;
  wherein said autonomous computational device is configured for being controlled by said peripheral device and for receiving said data from said sensor for monitoring said human subject; and
  (c) an agent software configured for being operated by said autonomous computational device and for analyzing said data from said sensor. wherein said agent software is configured to determine whether a physiological parameter of said human subject has deteriorated according to an analysis of said data. and wherein said agent software is configured to provide an alert message to said human subject if said physiological parameter has deteriorated, wherein said agent software is situated at a remote server.

37. A system for non-invasive monitoring of a human subject arcording to claim 36, wherein said message comprises at least one member of the group consisting of: an identification of said physiological parameter, a description of a result of said analysis, a text message, a verbally audible message, an icon representing said physiological parameter, and an instruction to said subject to touch said sensor.

* * * * *

UNITED STATES PATENT AND TRADEMARK OFFICE
CERTIFICATE OF CORRECTION

PATENT NO. : 7,407,484 B2
APPLICATION NO. : 10/472752
DATED : August 5, 2008
INVENTOR(S) : Ronen Korman Page 1 of 1

It is certified that error appears in the above-identified patent and that said Letters Patent is hereby corrected as shown below:

In Claim 23, Column 13, Line 52 the word "d)" should read --(d)--.

In Claim 37, Column 16, Line 39 the word "arcording" should read --according--.

Signed and Sealed this

Thirtieth Day of June, 2009

JOHN DOLL
*Acting Director of the United States Patent and Trademark Office*